(12) United States Patent
Thallapuranam et al.

(10) Patent No.: US 9,676,816 B2
(45) Date of Patent: Jun. 13, 2017

(54) HEPARIN AFFINITY TAG AND APPLICATIONS THEREOF

(71) Applicant: THE BOARD OF TRUSTEES OF THE UNIVERSITY OF ARKANSAS, Little Rock, AR (US)

(72) Inventors: Suresh Kumar Thallapuranam, Fayetteville, AR (US); Srinivas Jayanthi, Fayetteville, AR (US); Jacqueline Morris, Fayetteville, AR (US); Alicia Brown, Springdale, AR (US); David McNabb, Fayetteville, AR (US); Ralph Henry, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 14/378,230

(22) PCT Filed: Jan. 21, 2014

(86) PCT No.: PCT/US2014/012340
§ 371 (c)(1),
(2) Date: Aug. 12, 2014

(87) PCT Pub. No.: WO2015/112121
PCT Pub. Date: Jul. 30, 2015

(65) Prior Publication Data
US 2016/0145597 A1    May 26, 2016

(51) Int. Cl.
| | | |
|---|---|---|
| *C12N 9/64* | (2006.01) | |
| *C07K 14/00* | (2006.01) | |
| *C07K 1/22* | (2006.01) | |
| *B01D 15/20* | (2006.01) | |
| *B01D 15/22* | (2006.01) | |
| *B01D 15/38* | (2006.01) | |
| *B01D 69/08* | (2006.01) | |
| *B01J 20/28* | (2006.01) | |
| *B01J 20/286* | (2006.01) | |

(52) U.S. Cl.
CPC ............ *C07K 1/22* (2013.01); *B01D 15/206* (2013.01); *B01D 15/22* (2013.01); *B01D 15/3809* (2013.01); *B01D 69/08* (2013.01); *B01J 20/286* (2013.01); *B01J 20/28078* (2013.01); *C07K 14/00* (2013.01); *C12N 9/6424* (2013.01); *C12Y 304/21043* (2013.01); *C07K 2319/20* (2013.01); *C07K 2319/50* (2013.01)

(58) Field of Classification Search
None
See application file for complete search history.

(56) References Cited

U.S. PATENT DOCUMENTS 7,595,374 B1    9/2009  Chang et al.

FOREIGN PATENT DOCUMENTS

| GB | 1539332 | 1/1979 |
| WO | 2005/014619 A2 | 2/2005 |
| WO | 2010/001414 A1 | 1/2010 |
| WO | 2011/119608 A1 | 9/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Notification of Transmittal of the International Search Report and the Written Opinion of the International Searching Authority for PCT/US2014/012340, mailed Oct. 6, 2014, 9 pages.
Notification of Transmittal of the International Search Report and the Written Opinion for PCT Application No. PCT/US2015/012074, mailed Apr. 10, 2015, 11 pages.
Fromm, J.R. et al., Pattern and Spacing of Basic Amino Acids in Heparin Binding Sites, Archives of Biochemistry and Biophysics, vol. 343, No. 1, Jul. 1, 1997, pp. 92-100, Article No. 66970147.
Morris, Jacqueline et at, Heparin Binding Peptide as a Novel Affinity Tag for Purification of Recombinant Proteins, Department of Chemistry and Biochemistry, Department of Biological Sciences, University of Arkansas, 26 pages.

* cited by examiner

*Primary Examiner* — Christian Fronda
(74) *Attorney, Agent, or Firm* — J. Clinton Wimbish; Smith Moore Leatherwood LLP

(57) ABSTRACT

In one aspect, affinity tags for recombinant protein purification are described herein which, in some embodiments, can mitigate or overcome disadvantages of prior affinity tag systems. In some embodiments, for example, affinity tags described herein permit efficient elution of desired recombinant proteins with simplified solution systems, such as alkali metal salt solutions. An affinity tag described herein comprises an amino acid sequence including a repeating amino acid unit of BXXXBXX, wherein B is an amino acid selected from the group consisting of histidine, lysine and arginine and X is an amino acid selected from the group consisting of amino acids other than histidine, lysine and arginine.

4 Claims, 8 Drawing Sheets

SEQUENCE LISTING

```
<160> NUMBER OF SEQ ID NOS: 10

<210> SEQ ID NO 1
<211> LENGTH: 32
<212> TYPE: PRT
<213> ORGANISM: Artificial Sequence
<220> FEATURE:
<223> OTHER INFORMATION: Designed amino acid sequence to act as an
      affinity tag for binding heparin.

<400> SEQUENCE: 1

Ala Ser Lys Ala Gln Lys Ala Gln Ala Lys Gln Trp Lys Gln Ala Gln
 1               5                  10                  15

Lys Ala Gln Lys Ala Gln Ala Lys Gln Ala Lys Gln Ala Lys Gln Trp
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Designed amino acid sequence to act as an
      affinity tag for binding heparin.

<400> SEQUENCE: 2

Ala Ser Arg Leu Asn Lys Ala Gln Ala Lys Gln Ala Lys Gln Ala Gln
 1               5                  10                  15

Lys Ala Gln Lys Ala Gln Ala Lys Gln Ala Lys Asn Ser Arg Gln Trp
            20                  25                  30

<210> SEQ ID NO 3
<211> LENGTH: 99
<212> TYPE: DNA
<213> ORGANISM: Artificial Sequence
<220> FEATURE:
<223> OTHER INFORMATION: Designed nucleic acid for coding the amino acid
      sequence of SEQ ID No.: 1.

<400> SEQUENCE: 3
atggcctcca agcacagaa agcccaagca aaacaatgga acaagccca gaaagcacaa         60 aaagcccaag cgaaacaagc aaaacaagcc aaacaatgg                             99

<210> SEQ ID NO 4
<211> LENGTH: 99
<212> TYPE: DNA
<213> ORGANISM: Artificial Sequence
<220> FEATURE:
<223> OTHER INFORMATION: Designed nucleic acid for coding the amino acid
      sequence of SEQ ID No.: 2.

<400> SEQUENCE: 4
atggcaagcc gtctgaataa agcacaggca aacaagcaa aacaggcaca gaaagcccag       60
aaagcgcagg ccaaacaggc gaaaaatagc cgtcagtgg                             99
```

-continued

```
<210> SEQ ID NO 5
<211> LENGTH: 38
<212> TYPE: PRT
<213> ORGANISM: Artificial Sequence
<220> FEATURE:
<223> OTHER INFORMATION: Designed amino acid sequence to act as an
      affinity tag for binding heparin.

<400> SEQUENCE: 5

Ala Ser Lys Ala Gln Lys Ala Gln Ala Lys Gln Trp Lys Gln Ala Gln
 1               5                  10                  15

Lys Ala Gln Lys Ala Gln Ala Lys Gln Ala Lys Gln Ala Lys Gln Trp
             20                  25                  30

Leu Val Pro Arg Gly Ser
         35

<210> SEQ ID NO 6
<211> LENGTH: 38
<212> TYPE: PRT
<213> ORGANISM: Artificial Sequence
<220> FEATURE:
<223> OTHER INFORMATION: Designed amino acid sequence to act as an
      affinity tag for binding heparin.

<400> SEQUENCE: 6

Ala Ser Arg Leu Asn Lys Ala Gln Ala Lys Gln Ala Lys Gln Ala Gln
 1               5                  10                  15

Lys Ala Gln Lys Ala Gln Ala Lys Gln Ala Lys Asn Ser Arg Gln Trp
             20                  25                  30

Leu Val Pro Arg Gly Ser
         35

<210> SEQ ID NO 7
<211> LENGTH: 117
<212> TYPE: DNA
<213> ORGANISM: Artificial Sequence
<220> FEATURE:
<223> OTHER INFORMATION: Designed nucleic acid for coding the amino acid
      sequence of SEQ ID No.: 5.

<400> SEQUENCE: 7
atggcctcca aagcacagaa agcccaagca aaacaatgga acaagcccca gaaagcacaa      60
aaagcccaag cgaaacaagc aaaacaagcc aaacaatggc tggtgcctcg tggatcc        117

<210> SEQ ID NO 8
<211> LENGTH: 117
<212> TYPE: DNA
<213> ORGANISM: Artificial Sequence
<220> FEATURE:
<223> OTHER INFORMATION: Designed nucleic acid for coding the amino acid
      sequence of SEQ ID No.: 6.

<400> SEQUENCE: 8
atggcaagcc gtctgaataa agcacaggca aacaagcaa aacaggcaca gaaagcccag       60
aaagcgcagg ccaaacaggc gaaaaatagc cgtcagtggc tggtgcctcg tggatcc        117

<210> SEQ ID NO 9
<211> LENGTH: 408
<212> TYPE: DNA
<213> ORGANISM: Rattus norvegicus

<400> SEQUENCE: 9
gagaaactgg gaaagctcca atattcactg gactatgact tccagaataa ccagctgttg     60
```

-continued

```
gtgggaatca tccaggctgc tgaactgccc gccctggaca tggggggtac atccgatcca    120
tacgtcaaag tcttcctgct gcctgacaaa aagaagaaat ttgagactaa agtccaccgg    180
aaaaccctca atccagtctt caatgaacaa tttactttca aggtacccta ctcggaatta    240
ggtggcaaaa ccctggtgat ggctgtgtat gactttgatc gcttctccaa gcacgacatc    300
atcggagagt tcaaagttcc tatgaacacc gtggattttg gccatgtgac cgaggagtgg    360
cgcgatctcc agagcgctga gaaactcgag caccaccacc accaccac                408

<210> SEQ ID NO 10
<211> LENGTH: 15
<212> TYPE: PRT
<213> ORGANISM: Artificial Sequence
<220> FEATURE:
<223> OTHER INFORMATION: Designed amino acid sequence to produce
      polyclonal antibodies against an affinity tag for binding heparin.

<400> SEQUENCE: 10

Gln Lys Ala Gln Lys Ala Gln Ala Lys Gln Ala Lys Gln Ala Cys
 1               5                  10                  15
```

HEPARIN AFFINITY TAG AND APPLICATIONS THEREOF

STATEMENT OF GOVERNMENT RIGHTS

The present invention was made with government support under National Institutes of Health (NIH) Grant Number P30 GM103450. The United Stated Government has certain rights to the present invention.

RELATED APPLICATION DATA

The present application is the national stage application under 35 U.S.C. §371 of International Application No. PCT/US2014/012340, filed Jan. 21, 2014.

FIELD

The present invention relates to affinity tags for protein purification and, in particular, to affinity tags binding heparin.

BACKGROUND

Overexpression and purification of recombinant proteins are of significant interest to the pharmaceutical and biochemical industries. Recombinant proteins, for example, are used in a variety of commercially important applications, including therapeutics, bioinsecticides, diagnostic kits and many others. Advances in recombinant deoxyribonucleic acid (DNA) technology and protein expression systems have rendered practical the production of proteins in significant quantities employing a variety of hosts. However, rapid and efficient purification of recombinant proteins remains a major challenge. Downstream purification of recombinant proteins can account for about 80% of total production cost. Therefore, cost-effective purification methods are of critical importance to pharmaceutical and biotechnology companies.

In this context, affinity chromatography is the method of choice for protein purification. This method involves addition of a selective affinity tag sequence to the target protein gene to generate the fusion gene. The fusion protein, produced by overexpression of the fusion gene in heterologous hosts, is purified by exploiting the highly specific binding characteristics of the affinity tag. The affinity tag is subsequently removed from the target recombinant protein. Several affinity tags such as polyhistidine, glutathione S-transferase, maltose binding protein, chitin, thioredoxin, small ubiquitin modifier protein (SUMO), N-utilization substance A (Nus A) and others have been popularly employed for recombinant protein purification. Nevertheless, common problems afflict these affinity tags, including decreased column capacity due to large molecular size of the affinity tags, high cost of elution solutes, tendency of the affinity tag(s) to be expressed as insoluble inclusion bodies, problems in recovery of cleaved affinity tags and difficulties in accurately maintaining the pH of solution used for protein elution.

SUMMARY

In one aspect, affinity tags for recombinant protein purification are described herein which, in some embodiments, can mitigate or overcome disadvantages of prior affinity tag systems. In some embodiments, for example, affinity tags described herein permit efficient elution of desired recombinant proteins with simplified solution systems, such as alkali metal salt solutions. An affinity tag described herein comprises an amino acid sequence including a repeating amino acid unit of BXXXBXX, wherein B is an amino acid selected from the group consisting of histidine, lysine and arginine and X is an amino acid selected from the group consisting of amino acids other than histidine, lysine and arginine. In some embodiments, for example, the amino acid sequence of the affinity tag includes the sequence of SEQ ID NO:1 or SEQ ID NO:2. Alternatively, an affinity tag described herein comprises an amino acid sequence selected from Table I, wherein B is an amino acid selected from the group consisting of histidine, lysine and arginine and X is an amino acid selected from the group consisting of amino acids other than histidine, lysine and arginine. Further, an affinity tag described herein, in some embodiments, selectively binds heparin.

Table I

| Amino acid sequences of affinity tags |
|---|
| XBXXBXXBXXBX |
| XBXXBXXBX |
| XBXBXBXXBXBXBXB |
| BBBBXXBBB |
| XBBBXXBBBX |
| XBBBXXXXBBBXXXXBBBX |
| XBXBXXBXBXXBXBX |
| XBXXBXBXXBXBXXBX |
| XBBBXXBBBX |
| XBXBXXXXXBXBX |
| XBXXBXXBX |
| XBBXBXXXBXXXBXB |
| XBXBXXXXBXXXBX |
| XBXXXBXBBBXBXXBXXXBX |
| XBXXXBXXBXXBX |
| XBBXXBXBBBX |
| XBBXBXBXXXBX |
| XBBXBXBBX |
| XBXXBXBBXXBX |
| XBXBXXXXBXXXBX |
| XBBXXBXBBBX |

In another aspect, recombinant protein compositions are described herein employing affinity tags for purification processes. A recombinant protein composition described herein comprises a first amino acid sequence of a target protein and an affinity tag coupled to the first amino acid sequence, the affinity tag comprising an amino acid sequence for binding heparin. The amino acid sequence of the affinity tag can comprise a repeating amino acid unit of BXXXBXX, wherein B is an amino acid selected from the group consisting of histidine, lysine and arginine and X is an amino acid selected from the group consisting of amino acids other than histidine, lysine and arginine. For example, the amino acid sequence of the affinity tag can include the sequence of SEQ ID NO:1 or SEQ ID NO:2. Moreover, in other embodiments, the amino acid sequence of the affinity tag can comprise an amino acid sequence selected from Table I. Further, a protease cleavage site can be positioned between the first amino acid sequence of the target protein and the affinity tag amino acid sequence. In some embodiments, a suitable protease cleavage site is a serine protease cleavage site or cysteine protease cleavage site.

Recombinant DNA encoding protein compositions described herein are also provided. A recombinant DNA molecule, for example, encodes an amino acid sequence of a target protein and associated affinity tag amino acid sequence for binding heparin. The encoded amino acid sequence for binding heparin comprises a repeating amino acid unit of BXXXBXX, wherein B is an amino acid selected from the group consisting of histidine, lysine and arginine and X is an amino acid selected from the group consisting of amino acids other than histidine, lysine and arginine. In some embodiments, the recombinant DNA molecule comprises the nucleotide sequence of SEQ ID NO:3 or SEQ ID NO:4 encoding the amino acid sequence of the affinity tag. Additionally, in some embodiments, the encoded amino acid sequence for binding heparin comprises an amino acid sequence selected from Table I.

In another aspect, methods of purifying recombinant protein compositions are described herein. A method of purifying a recombinant protein composition comprises providing a mixture including the recombinant protein composition, the recombinant protein composition comprising a first amino acid sequence of a target protein and an affinity tag coupled to the first amino acid sequence, the affinity tag comprising an amino acid sequence for binding heparin. The mixture is loaded onto a separation column having a stationary phase comprising heparin, and the recombinant protein is bound to the heparin stationary phase via the affinity tag. The bound recombinant protein is subsequently eluted from the column. In some embodiments, the mixture comprising the recombinant protein composition is a lysate, such as that from the expressing host.

As described herein, the affinity tag amino acid sequence for binding heparin can comprise a repeating amino acid unit of BXXXBXX, wherein B is an amino acid selected from the group consisting of histidine, lysine and arginine and X is an amino acid selected from the group consisting of amino acids other than histidine, lysine and arginine. Additionally, in some embodiments, the amino acid sequence for binding heparin comprises an amino acid sequence selected from Table I. Further, a protease cleavage site can be positioned between the first amino acid sequence of the target protein and the affinity tag amino acid sequence. Therefore, the affinity tag can be cleaved from the recombinant protein at the cleavage site with suitable protease.

In a further aspect, separation media are described herein which can be used in the purification of protein compositions. A separation medium described herein comprises a support phase and a stationary phase attached to the support phase, the stationary phase including an amino acid sequence comprising a repeating amino acid unit of BXXXBXX, wherein B is an amino acid selected from the group consisting of histidine, lysine and arginine and X is an amino acid selected from the group consisting of amino acids other than histidine, lysine and arginine. In some embodiments, for example, the amino acid sequence comprises the sequence of SEQ ID NO:1 or SEQ ID NO:2. In other embodiments, the stationary phase can include an amino acid sequence selected from Table I. The amino acid sequence of the stationary phase can be operable to selectively bind heparin. Additionally, the amino acid sequence can be attached to the stationary phase through a spacer.

Methods of purifying heparin are also described herein. A method of purifying heparin comprises providing a mixture including heparin and loading the mixture onto a separation column comprising a support phase and a stationary phase attached to the support phase, the stationary phase including an amino acid sequence comprising a repeating amino acid unit of BXXXBXX, wherein B is an amino acid selected from the group consisting of histidine, lysine and arginine and X is an amino acid selected from the group consisting of amino acids other than histidine, lysine and arginine. In some embodiments, the stationary phase amino acid sequence comprises the sequence of SEQ ID NO:1 or SEQ ID NO:2. Alternatively, the stationary phase can include an amino acid sequence selected from Table I. Heparin from the mixture is bound to the stationary phase and subsequently eluted from the column.

In a further aspect, polyclonal antibodies are provided for recognizing affinity tags described herein. In some embodiments, a composition comprises polyclonal antibodies recognizing the amino acid sequence of SEQ ID NO:10. For example, the polyclonal antibodies can be bound to an antigen comprising an amino acid sequence incorporating SEQ ID NO:10. Moreover, the antigen can be an affinity tag further comprising a repeating amino acid unit of BXXXBXX, wherein B is an amino acid selected from the group consisting of histidine, lysine and arginine and X is an amino acid selected from the group consisting of amino acids other than histidine, lysine and arginine. Additionally, the affinity tag can be coupled to a target protein as described herein.

These and other embodiments are described further in the detailed description which follows.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

I. Affinity Tags

In one aspect, affinity tags for recombinant protein purification are described herein. An affinity tag described herein comprises an amino acid sequence including a repeating amino acid unit of BXXXBXX, wherein B is an amino acid selected from the group consisting of histidine, lysine and arginine and X is an amino acid selected from the group consisting of amino acids other than histidine, lysine and arginine In some embodiments, for example, X is an amino acid selected from Table II.

TABLE II

| Amino Acids of X |
|---|
| Alanine |
| Asparagine |
| Aspartic Acid |
| Cysteine |
| Glutamic Acid |
| Glutamine |
| Glycine |
| Isoleucine |
| Leucine |
| Methionine |
| Phenylalanine |
| Proline |
| Serine |
| Threonine |
| Tryptophan |
| Tyrosine |
| Valine |

Figure 1:
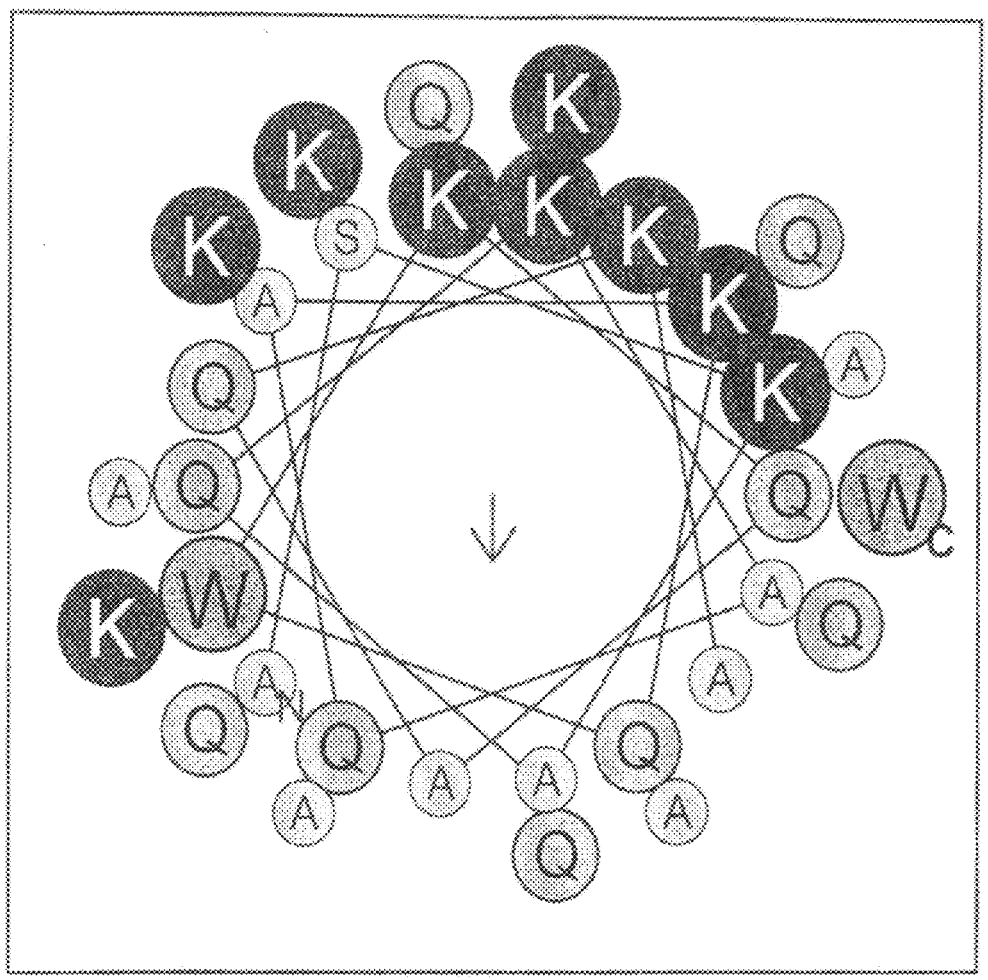
FIG. 1 is a pep-wheel diagram of an affinity tag according to one embodiment described herein.

The amino acid unit of BXXXBXX, in some embodiments, repeats at least three times in the affinity tag amino acid sequence. The amino acid unit can repeat sequentially or amino acid(s) can be positioned between the individual repeating amino acid units. For example, an affinity tag can include the generic sequence of -XXBXXBXXXBXX-BXXXBXXBXXXBXXBXXBXX-, wherein X and B are defined above. Alternatively, an affinity tag described herein comprises an amino acid sequence selected from Table I. Selection of specific amino acids for X and B can be governed by the intended functionality of the amino acid sequence in the affinity tag. For example, the amino acid sequence can be employed to bind heparin. In such embodiments, X and B can be selected to produce a peptide structure having high propensity to form an amphipathic helix, wherein side chains of the polar and non-polar amino acids are oriented on opposite sides of the helix. Moreover, polar amino acids of the sequence should have suitable locations for forming electrostatic interactions with heparin. Further, more than about 60% of the amino acids chosen for the generic sequence should be polar to facilitate overexpression of recombinant-affinity tag proteins in the soluble form. In view of these considerations, the generic amino acid sequence, in some embodiments, can have the specific sequence of SEQ ID NO:1 or SEQ ID NO:2. FIG. 1 is a pep-wheel diagram of the amino acid sequence of SEQ ID NO:1 illustrating the foregoing design principles for heparin binding. As illustrated in FIG. 1, the resulting peptide displays an asymmetric distribution of the polar and non-polar amino acids, wherein N and C represent the N- and the C-terminal ends of the peptide.

As provided further herein, affinity tags having amino acid sequences and structure described in this Section I can be expressed from recombinant DNA encoding for the sequence. For example, SEQ ID:3 is the nucleotide sequence encoding the amino acid sequence of SEQ ID NO:1. Similarly, SEQ ID:4 is the nucleotide sequence encoding the amino acid sequence of SEQ ID NO:2. Alternatively, affinity tags having amino acid sequences described herein can be synthesized by solid-state methods known to those of skill in the art. Solid-state synthesis of the affinity tags can find applicability in separation media described below.

II. Recombinant Protein Compositions and Recombinant DNA

In another aspect, recombinant protein compositions are described herein employing affinity tags for purification processes. A recombinant protein composition described herein comprises a first amino acid sequence of a target protein and an affinity tag coupled to the first amino acid sequence, the affinity tag comprising an amino acid sequence for binding heparin. The affinity tag can employ any amino acid sequence suitable for binding heparin. In some embodiments, the affinity tag comprises an amino acid sequence described in Section I above. For example, the affinity tag can include an amino acid sequence comprising a repeating amino acid unit of BXXXBXX, wherein B and X are defined in Section I herein. In particular embodiments, the affinity tag includes the sequence of SEQ ID NO:1 or SEQ ID NO:2. Moreover, in other embodiments, the amino acid sequence of the affinity tag can comprise an amino acid sequence selected from Table I.

Further, a protease cleavage site can be positioned between the first amino acid sequence of the target protein and the affinity tag amino acid sequence. Any protease cleavage site or restriction site not inconsistent with the objectives of the present invention can be used for cleavage of the affinity tag from the recombinant target protein. In some embodiments, a suitable protease cleavage site is designed for serine protease(s). A serine protease cleavage site, for example, may be constructed for use with thrombin. SEQ ID NO:5 and SEQ ID NO:6 each provide a specific affinity tag amino acid sequence coupled to a thrombin cleavage site. Alternatively, a cleavage site can be constructed for cysteine protease(s). A cysteine protease cleavage site, for example, may be constructed for use with tobacco etch virus (TEV) protease. Other suitable protease cleavage or restriction sites can include factor Xa, enterkinase and peptides modified with cyanogen bromide. Identity of cleavage site is not a limiting factor for employment of affinity tags described herein.

Recombinant DNA encoding the target protein and associated affinity tag is inserted into a host for overexpression. The recombinant DNA molecule, for example, can encode any affinity tag amino acid sequence described in Section I above. In some embodiments, the recombinant DNA molecule encodes an affinity tag amino acid sequence comprising a repeating amino acid unit of BXXXBXX, wherein B is an amino acid selected from the group consisting of histidine, lysine and arginine and X is an amino acid selected from Table II herein. The recombinant DNA molecule can encode for the amino acid unit to be repeated at least three times in the affinity tag sequence. In a particular embodiment, the recombinant DNA encodes an affinity tag amino acid sequence of SEQ ID NO:1. In such an embodiment, the recombinant DNA molecule includes the nucleotide sequence of SEQ ID NO:3. In another embodiment, the recombinant DNA can encode an affinity tag amino acid sequence of SEQ ID NO:2 and include a nucleotide sequence of SEQ ID NO:4. Additionally, in some embodiments, the recombinant DNA molecule encodes an affinity tag amino acid sequence comprising a sequence selected from Table I. Recombinant DNA encoding affinity tags described herein can be artificially synthesized according to techniques known to one of skill in the art.

In addition to the target protein and the affinity tag, the recombinant DNA molecule may encode for a protease cleavage site between the target protein and affinity tag. As described herein, a serine or cysteine protease cleavage site can be employed for cleavage of the affinity tag subsequent to purification of the recombinant protein. For example, the recombinant DNA molecule can encode the amino acid sequence of SEQ ID NO:5. In such an embodiment, the recombinant DNA molecule comprises the nucleotide sequence of SEQ ID NO:7. Alternatively, the recombinant DNA molecule can encode the amino acid sequence of SEQ ID NO:6, thereby including the nucleotide sequence of SEQ ID NO:8.

Figure 2:
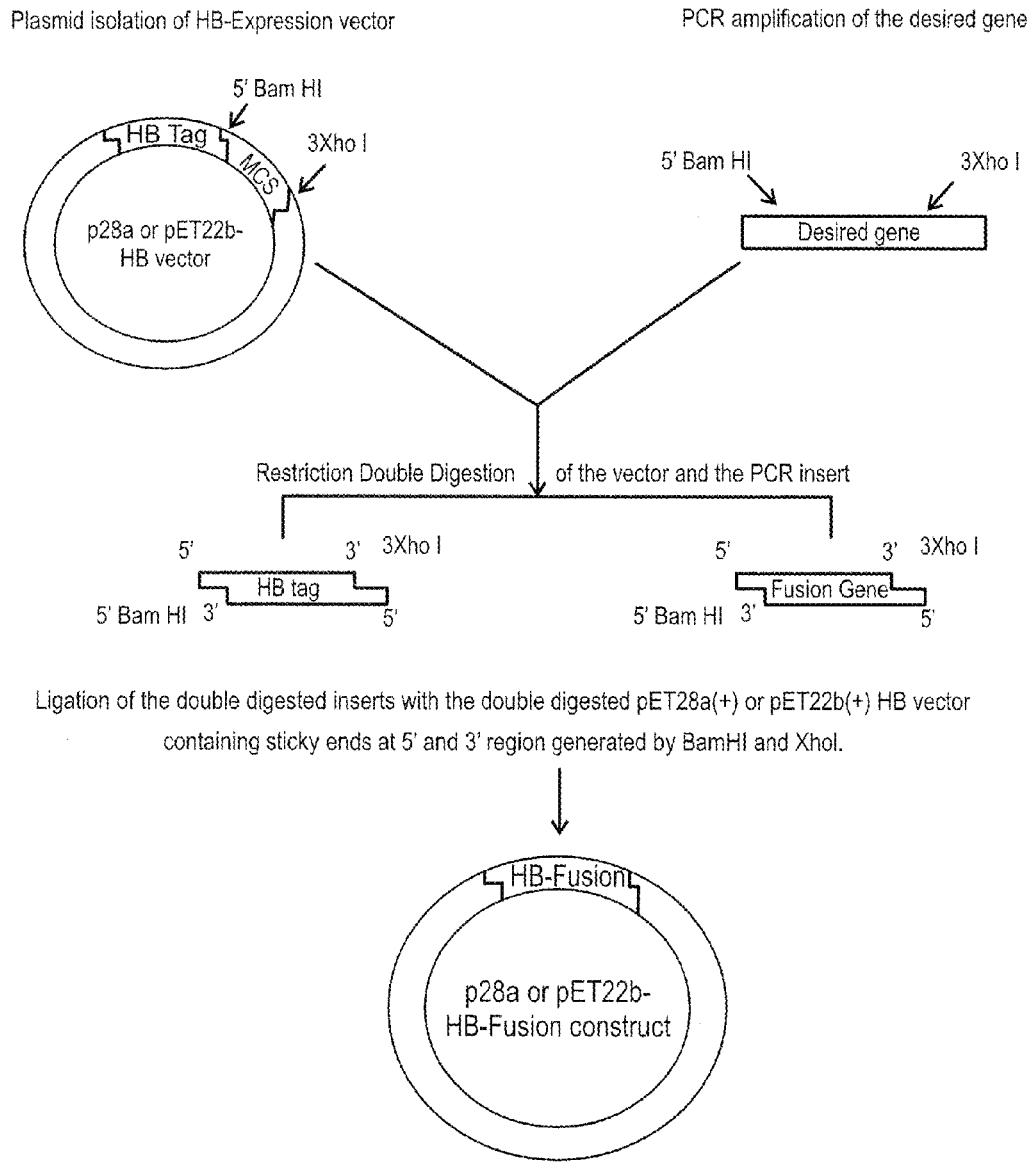
FIG. 2 illustrates a synthetic pathway for a plasmid encoding a target protein and associated heparin binding (HB) affinity tag according to one embodiment described herein.

Various vectors encoding the target protein, associated affinity tag and protease cleavage site can be employed. For example, plasmids or viral vectors can be used. Alternatively, yeast or mammalian vectors can be used. Appropriate amplification techniques and restriction enzymes are used to construct vectors for expression of the target protein and associated affinity tag by a host. Moreover, the vector can include control sequences such as promoter sequences. Expression control sequences of the vector can vary depending on whether the vector is designed to express a nucleotide sequence in a prokaryotic or eukaryotic host. Expression control sequences may include transcriptional regulatory elements such as promoters, enhancer elements and transcriptional termination sequences, and/or translational regulatory elements, such as translational initiation and termination sites. FIG. 2 illustrates construction of a vector encoding a target protein and associated heparin binding affinity tag according to an embodiment described herein. As illustrated in FIG. 2, plasmid pET28a (or plasmid pET22b) containing the affinity tag for binding heparin is digested with restriction enzymes Bam HI and XhoI. Genes containing the target protein are also digested with restriction enzymes Bam HI and XhoI. The gene inserts subsequently undergo ligation with the doubly digested pET28a (or pET22b) vector to complete vector construction. As described herein, the vector can also include a protease cleavage site between the affinity tag and target protein.

Once the vector encoding the target protein, affinity tag and protease cleavage site is prepared, the vector is introduced into an appropriate host cell by any of a variety of suitable techniques, including transformation as known in the art. In some embodiments, for example, the constructed vector is inserted into bacterial host(s) such as *Escherichia coli*. After transformation, recipient cells are grown in an appropriate medium and overexpression of the target protein is administered.

III. Recombinant Protein Purification

In another aspect, methods of purifying recombinant protein compositions are described herein. A method of purifying a recombinant protein composition comprises providing a mixture, such as a lysate, including the recombinant protein composition, the recombinant protein composition comprising a first amino acid sequence of a target protein and an affinity tag coupled to the first amino acid sequence, the affinity tag including an amino acid sequence for binding heparin. In some embodiments, the affinity tag comprises an amino acid sequence described in Section I above. For example, the affinity tag can include an amino acid sequence comprising a repeating amino acid unit of BXXXBXX, wherein B and X are defined in Section I herein. In particular embodiments, the affinity tag includes the sequence of SEQ ID NO:1 or SEQ ID NO:2. Moreover, the affinity tag can include an amino acid sequence selected from Table I.

The mixture is loaded onto a separation column having a stationary phase comprising heparin and the recombinant protein is bound to the heparin stationary phase via the affinity tag with the unbound fraction passing through the column. The bound recombinant protein is subsequently eluted from the column. Elution of the recombinant protein, in some embodiments, is achieved with an alkali metal salt gradient. For example, a sodium chloride (NaCl) gradient can be used for elution of the bound recombinant protein. Other suitable salt eluents not inconsistent with the objectives of the present invention are also contemplated. The eluted recombinant protein can demonstrate purity in excess of 90%. In some embodiments, the eluted recombinant protein is at least 95% pure.

A cleavage site is positioned between the heparin binding affinity tag and target protein. A serine or cysteine protease cleavage site, for example, can be employed for cleavage of the affinity tag from recombinant protein subsequent to protein purification. For example, a thrombin cleavage site as set forth in sections of amino acid sequences SEQ ID NO:5 and SEQ ID NO:6 can be used. The heparin binding affinity tag is cleaved from the recombinant protein, and the resulting mixture is loaded to a separation column comprising heparin stationary phase. The affinity tag is bound to the heparin stationary phase and the recombinant protein passes through the column as a purified unbound fraction.

EXAMPLE

Bacterial expression vector pET28a was modified as follows to include the nucleotide sequence of SEQ ID NO:7 encoding a heparin binding (HB) affinity tag and thrombin cleavage site and the nucleotide sequence of SEQ ID NO:9 encoding the C2A domain of rat synaptotagmin. SEQ ID NO:7 was cloned into pET28a, and the resulting plasmid was isolated using the Qiagen Mininprep Plasmid Purification kit. Approximately 5 μg of plasmid was obtained from 3 mL of bacterial culture that was incubated overnight at 37° C. under constant stirring conditions (250 rpm) with suitable antibiotic. Using gene specific primers with the desired restriction sites (BamHI and XhoI), genes corresponding to C2A (SEQ ID NO:9), S100A13 and C-termAlb3 were amplified using the Phusion PCR Mastermix with an appropriate DNA template. Polymerase chain reaction (PCR) conditions employed were consistent with the protocol provided by the vendor. Annealing temperature for optimal primer binding was appropriately set for each clone (62.5° C. for C2A, 64° C. for S100A13 and 62.4° C. for C-termAlb3). After successful amplification of the gene inserts, PCR products were subjected to cleanup using the Qiagen PCR cleanup kit. Further, double digestion of the inserts and HB modified pET28a plasmid was administered with BamHI and XhoI. The double-digested pET28a plasmid was subjected to dephosphorylation reaction using Antarctic phosphatase enzyme. The dephosphorylated pET28a plasmid and double digested inserts, including C2A, were resolved on 1% agarose gel followed by gel extraction and elution. Ligation of the C2A insert and HB modified pET28a plasmid was subsequently performed using T4 ligase at 22° C. for 20 minutes. The ligation product was used to carry-out transformation of chemically competent DH5α cells, which were plated on agar plates with suitable antibiotic. After an incubation period of 14-16 hours, transformations observed on the plates were subjected to screening by colony PCR method using Taq polymerase. Plasmids from positive colonies were then isolated and confirmed both by double digestion and DNA sequencing.

Figure 3:
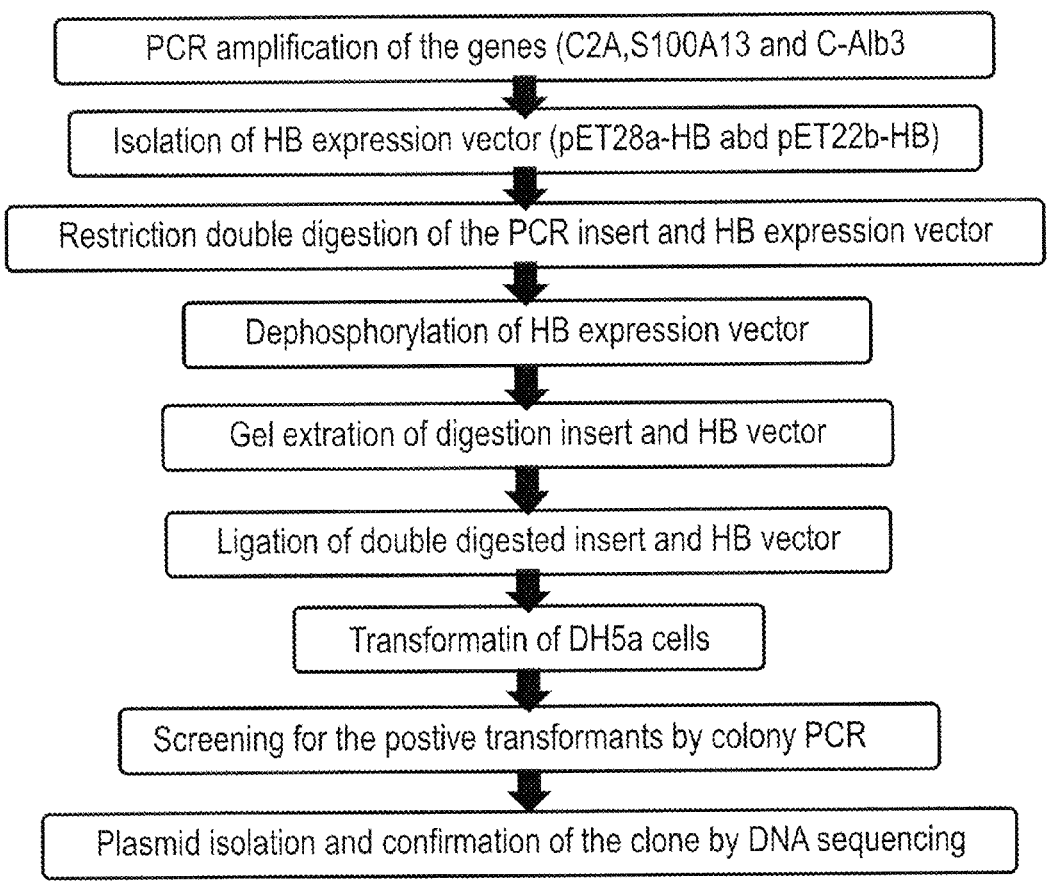
FIG. 3 is a flow chart illustrating a synthetic pathway for a plasmid encoding a target protein and associated heparin binding (HB) affinity tag according to one embodiment described herein.

FIG. 3 is a flow chart illustrating the foregoing synthesis. Further, as illustrated in FIG. 2, bacterial vector pET22b can also be modified to include the nucleotide sequence of SEQ ID NO:7 encoding a HB affinity tag and thrombin cleavage site and the nucleotide sequence of SEQ ID NO:9 encoding the C2A domain of rat synaptotagmin. Use of pET28a and pET22b permits selection of the antibiotic resistance [ampicillin(pET22b) or kanamycin(pET28a)] and also the frame for cloning genes in multiple cloning sites (MCS).

Overexpression

The pET28a plasmid encoding the heparin binding affinity tag (HB), thrombin cleavage site and C2A domain of rat synaptotagmin was transformed into BL21(DE3) cells. Overexpression of the HB-fused C2A target protein was administered in LB medium. Bacterial cells were allowed to grow in a suitable antibiotic medium until the OD reached 0.4-0.5. Upon reaching the desired OD, cells were induced with 1 mM IPTG and were allowed to grow for an additional time period of 4 hours. Cells were later harvested by centrifugation under refrigerated conditions (at 4° C.) at 6000 rpm.

Purification

Overexpressed bacterial cells were lysed by subjecting the cells to three passes through the French Cell Press followed by 10 cycles of sonication (with 10 seconds each in the on-phase and off-phase in ice with an amplitude of 3 and 11 watts output). Overexpression of the HB-fused C2A (HB-C2A) revealed that the protein was predominantly expressed in the soluble form in the supernatant of the *E. coli* lysate. Purification of the HB-C2A target protein from the lysate was achieved using a heparin sepharose column. Elution of the HB-C2A target protein was monitored by 280 nm absorbance of the HB affinity tag. Protein elution was administered using a stepwise gradient of NaCl dissolved in 10 mM tris-HCl buffer (pH 7.2-8.0) according to Table III.

TABLE III

| Stepwise NaCl Elution Gradient |
| --- |
| 100 mM |
| 250 mM |
| 350 mM |
| 500 mM |
| 750 mM |
| 1000 mM |
| 1500 mM |

Figure 4:
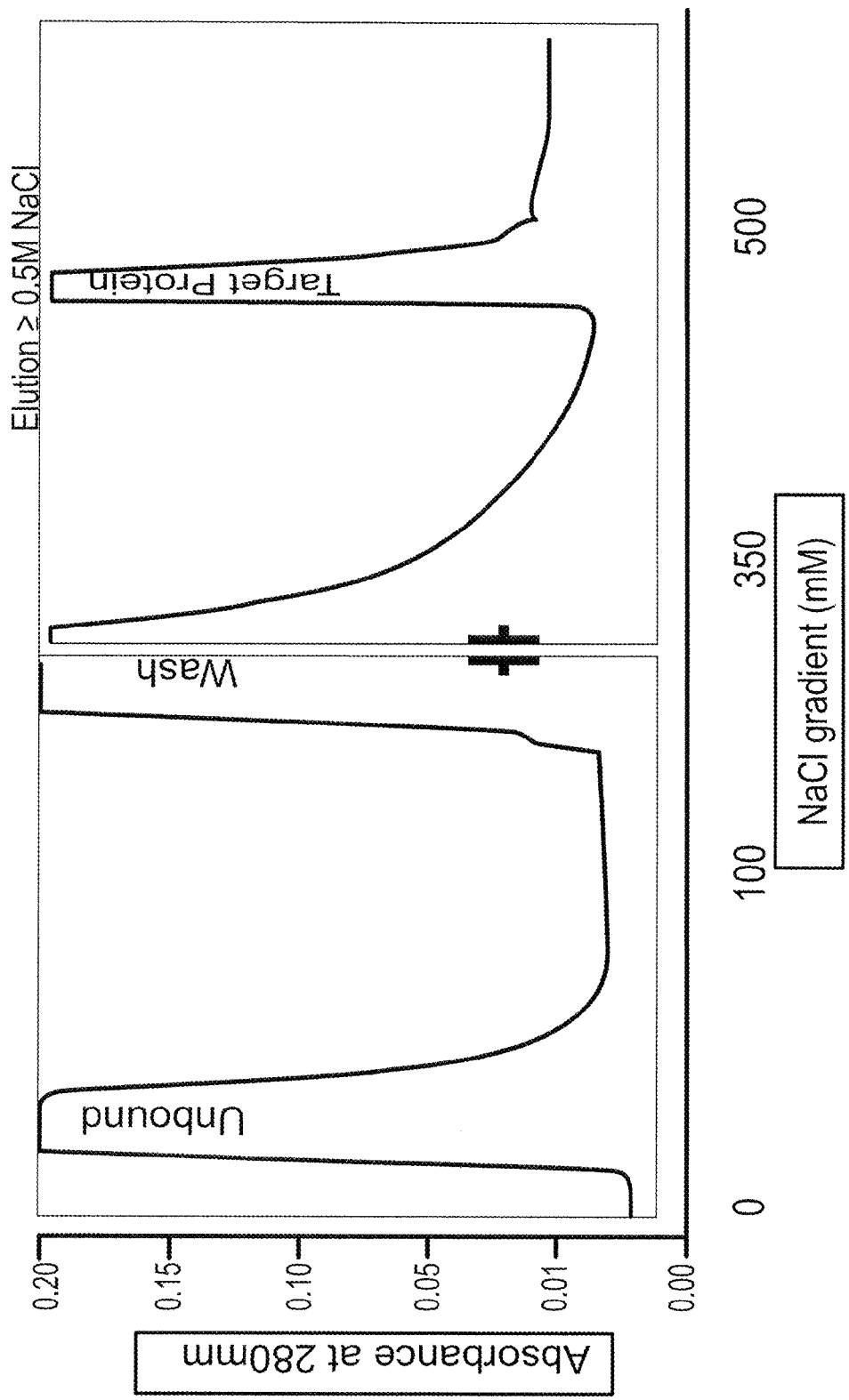
FIG. 4 illustrates an elution profile of bound and unbound fractions in response to a NaCl gradient according to one embodiment described herein.

FIG. 4 illustrates the elution profile of bound and unbound fractions in response to the NaCl gradient. Results of SDS-PAGE showed that most of the proteins in the soluble portion of the *E. coli* lysate eluted as an unbound fraction in low NaCl (≥100 mM) concentration. HB-C2A bound to the heparin stationary phase consistently eluted at 500 mM NaCl and was more than ~95% pure (as assessed by staining of the SDS-PAGE gels independently with Coomassie blue and silver). SDS-PAGE protocol is described below.

Figure 5:
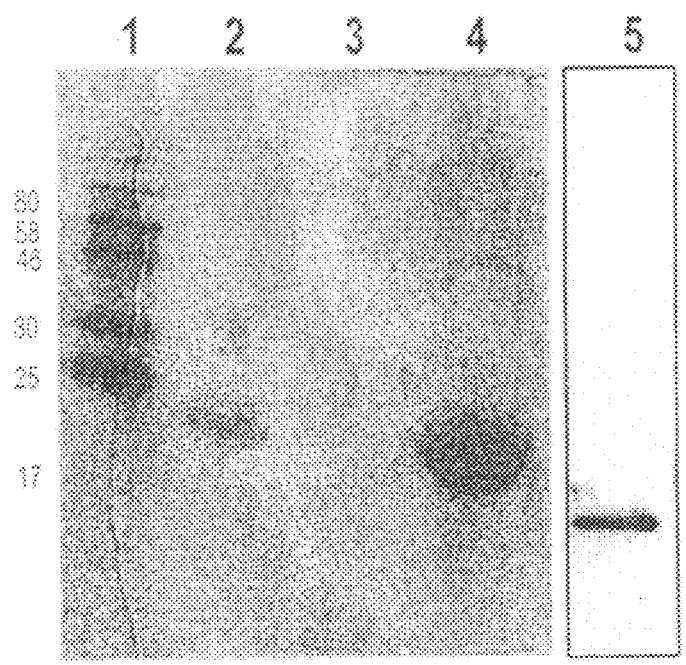
FIG. 5 is a Western blot of protein fractions eluted from a heparin sepharose column using a stepwise salt gradient according to one embodiment described herein.

Further, the gel containing the fusion proteins was subjected to blot transfer for Western blot and dot blot analyses. Western blot and dot blot protocol, including generation of HB-antibodies, is described below. FIG. 5 illustrates results of the Western blotting with lanes identified in Table IV.

TABLE IV

| Western Blot Lane Identification | |
| --- | --- |
| Lane | Identification |
| 1 | Protein marker |
| 2 | HB-C2A whole lysate |
| 3 | HB-C2A insoluble pellet |
| 4 | Purified HB-C2A |
| 5 | Purified HB-S100A13* |

*Provided as an additional example of target protein bound to HB affinity tag

Figure 6:
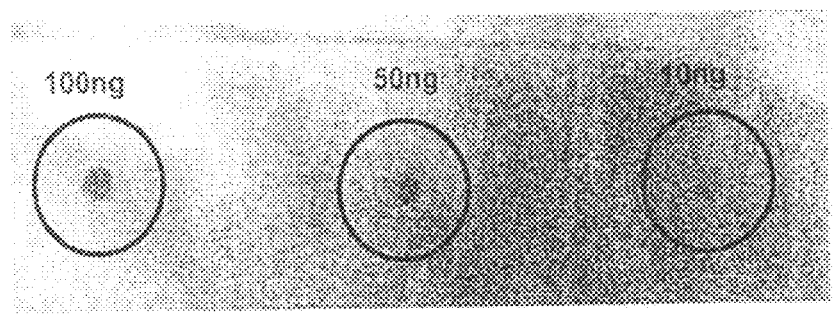
FIG. 6 is a dot blot demonstrating limits of detection of a target protein and associated heparin binding affinity tag according to an embodiment described herein.

FIG. 6 illustrates results of the dot blot analysis. As illustrated in FIG. 6, HB-C2A was detectable in amounts less than 10 ng.

Fractions containing the HB-C2A target protein were desalted by constant dialysis against 10 mM phosphate buffer (pH 6.5) containing 100 mM NaCl. The protein sample was concentrated down to 2-3 mL, and cleavage of the HB-tag from the C2A target was achieved by incubation of the HB-C2A target protein with one unit of thrombin per 25 μg of target protein at 37° C. for 20-24 hours in 10 mM tris-HCL containing 100 mM NaCl. The thrombin-induced cleavage reaction was stopped by the addition of 0.2M phenylmethyl sulfonylfluoride (PMSF, 1 μL per mL of the reaction mixture). The cleavage products of the thrombin reaction were separated by passing them through a 2-mL heparin sepharose spin column. The target C2A protein was eluted in the wash buffer [10 mM tris-HCl (pH 7.2) containing 100 mM NaCl]. The bound HB affinity tag eluted in 10 mM tris-HCl (pH 7.2) buffer containing 500 mM NaCl and was 95% pure.

Characterization

Figure 7:
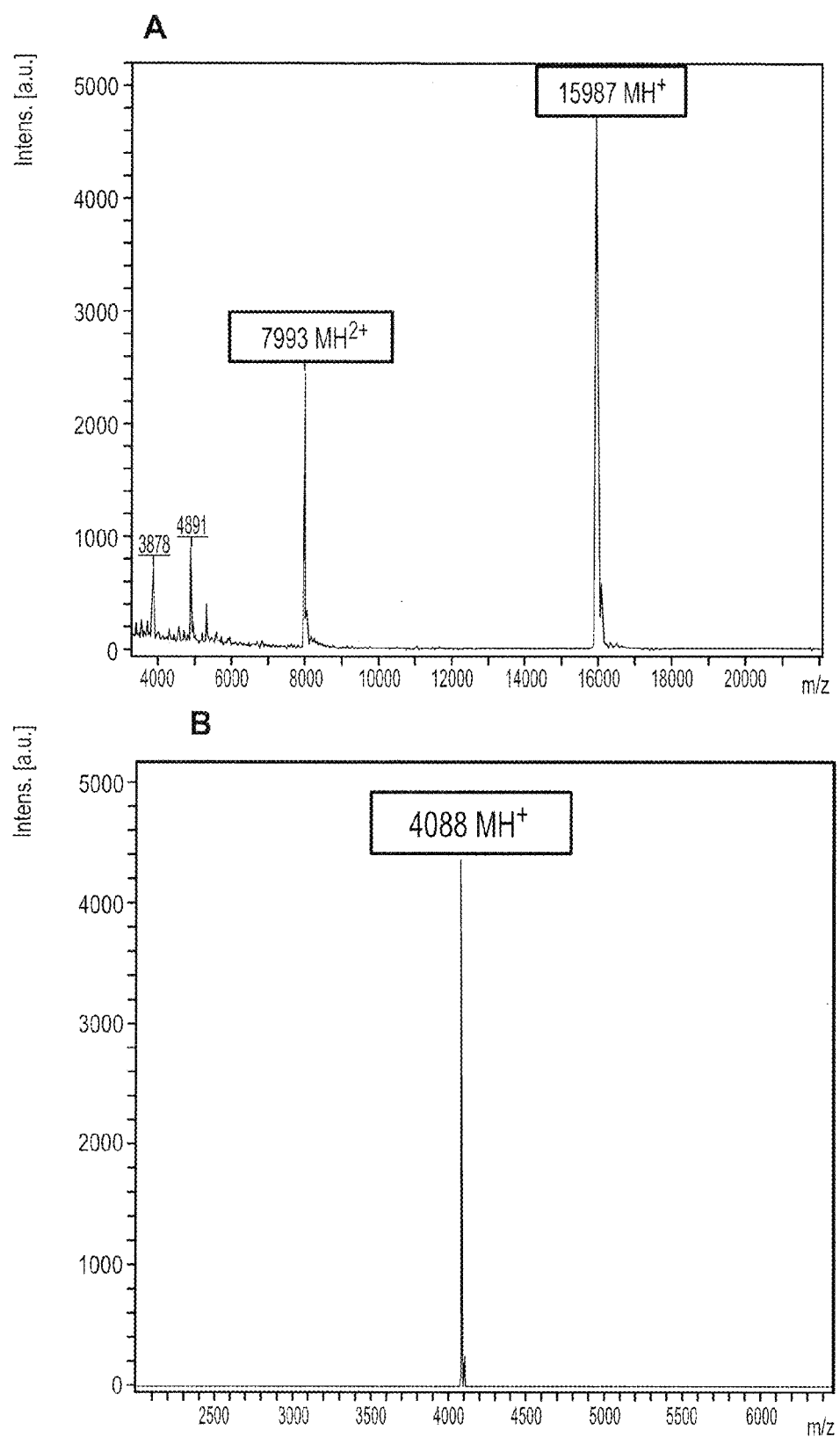
FIG. 7 provides mass spectrometry results identifying (A) the target protein and (B) heparin binding affinity tag according to one embodiment described herein.

MALDI-MS was performed on the purified target protein and the HB affinity-tag to check both their purity and their molecular weights. All mass spectrometry experiments were acquired at the Statewide Mass Spectrometry facility located at the University of Arkansas, Fayetteville. MALDI mass results provided in FIG. 7 displayed the expected mass for both the HB affinity tag (Mr 4088Da) and the recombinant C2A domain (Mr 15987Da).

Figure 8:
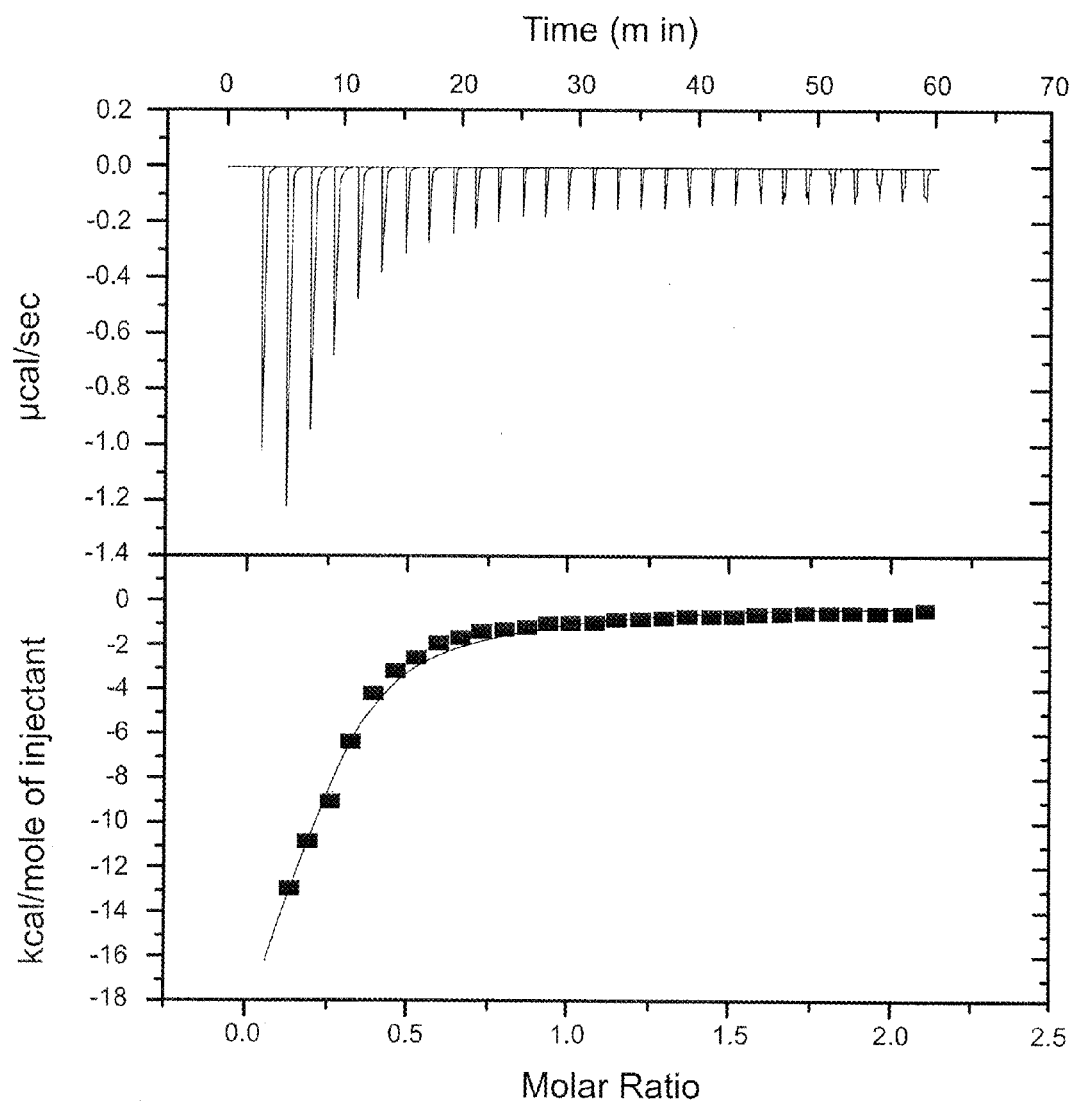
FIG. 8 is an isothermogram depicting titration of the HB affinity tag with heparin.

Isothermal titration calorimetry (ITC) experiments were performed to measure the heparin binding affinity of the purified HB affinity tag. ITC experiments were performed using the iTC200 (MicroCal Inc., Northampton, Mass.) at 25° C. The HB-tag, in 10 mM phosphate buffer (pH 7.2) containing 100 mM NaCl, was centrifuged to remove possible water insoluble material and later degassed before titration. Concentrations of heparin to HB-tag were maintained at a ratio of 10:1. The contents of the syringe (heparin) were added sequentially in 1.3 μl aliquots to the cell (HB-tag) with a 12 sec interval. The raw ITC data were analyzed using Origin Version 7.0 software provided by the vendor (MicroCal Inc. Northhampton, Mass.). Heats of reaction per injection (μcalories/sec) were determined by the integration of peak areas. Thermodynamic (ΔG, ΔH, and ΔS) and binding parameters [dissociation constant (Kd) and binding stoichiometry (n)] were calculated by fitting the raw data to a one-site of binding model available in Origin 7.0. ITC results demonstrated that HB affinity tag has a nanomolar binding affinity for heparin ($K_d$~190 nM) and the HB-heparin binding proceeds with the evolution of heat (ΔH=−1.158E$^5$) suggesting that the interaction is largely electrostatic. The binding stoichiometry between HB affinity tag and heparin was 1:1. FIG. 8 is an isothermogram depicting the titration of the HB affinity tag with heparin. The upper panel illustrates the raw isothermogram and the lower panel is the best-fit binding curve using the multiple site binding model provided by GE Healthcare, Inc.

Figure 9:
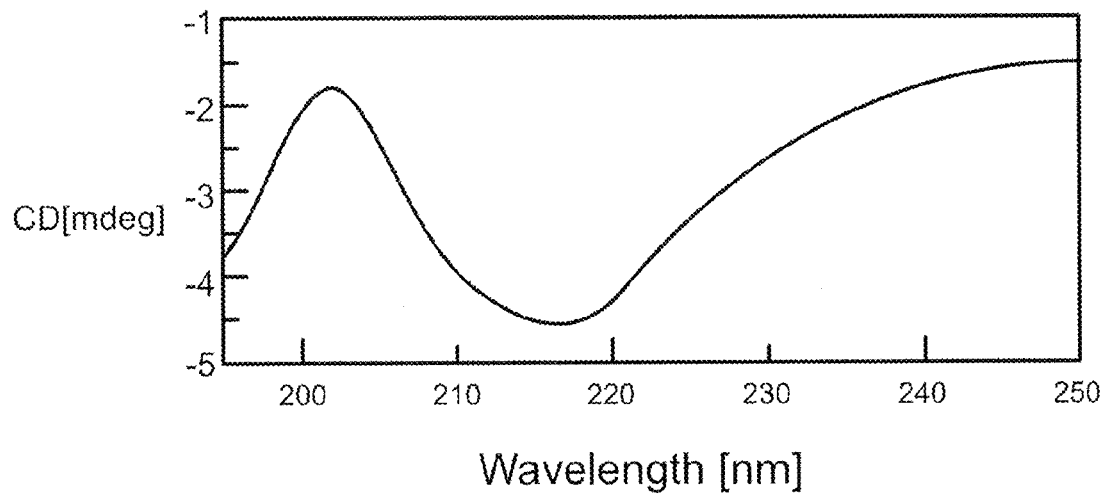
FIG. 9 is a far UV circular dichroism (CD) spectrum of a purified target protein according to one embodiment described herein.
Figure 10:
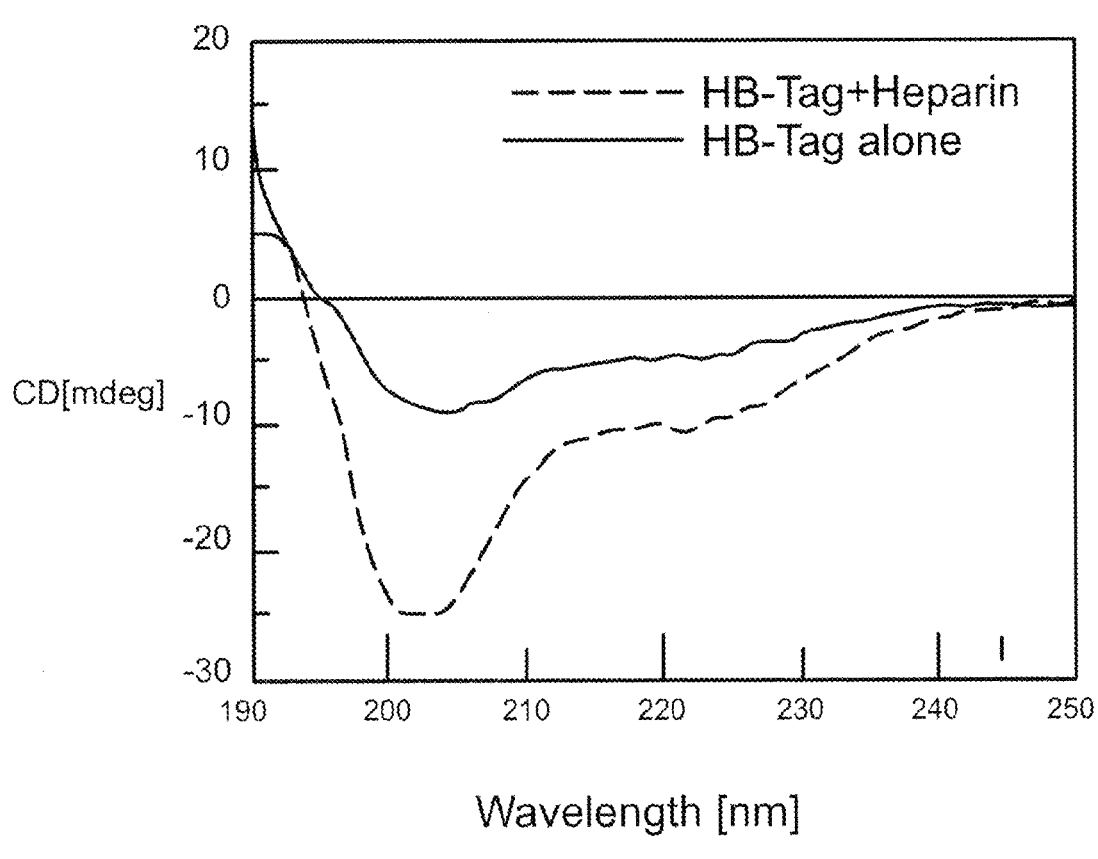
FIG. 10 are far UV CD spectra of a heparin binding affinity tag in an unbound state and a heparin bound state according to one embodiment described herein.

Far UV circular dichroism (CD) spectra were acquired using a Jasco J720 spectropolarimeter. CD data were acquired at 25° C. using a 0.1 mm pathlength quartz cell. CD experiments were performed by dissolving the protein/peptide samples (~150 μM) in 10 mM phosphate buffer (pH 7.0) containing 100 mM NaCl. All CD spectra are an average of 10 scans acquired with a scan speed of 50 nm/second. All CD data were corrected for background absorbance. As shown in FIG. 9, the far UV circular dichroism (CD) spectrum of the purified recombinant C2A domain showed a negative ellipticity centered at 218 nm suggesting that the backbone of the protein is predominantly in a helical conformation. The far UV CD spectrum of the purified recombinant C2A domain also showed a perfect match with the published spectrum of the C2A domain indicating that the purified protein is in its native conformation. The far UV spectrum of purified HB affinity tag (obtained after thrombin cleavage of recombinant HB-C2A) of FIG. 10 displayed a negative CD band at around 202 nm suggesting that it is in a disordered conformation. In the presence of heparin, however, the HB affinity tag underwent a major backbone conformational change from a disordered state to a helical conformation. The backbone conformational change is reflected in the appearance of the helix-characteristic double minima, located at 208 nm and 222 nm, in the far UV CD spectrum of the HB affinity tag obtained in the presence of heparin. The heparin-induced disordered state to helix transition plausibly suggests that the HB affinity tag can bind to heparin in the disordered state(s) and this property can be successfully exploited to recover and purify HB-tagged recombinant proteins from inclusion bodies.

HB-antibodies (HB-Ab) for Western blotting were generated by Genescript, N.J., USA per submitted specifications. The segment of the HB tag possessing the highest antigenicity was designed using the Optimum Antigen design program at the vendor's site (http://www.genscript.com/PolyExpress.html). HB-Ab was raised in rabbits against the HB peptide sequence of SEQ ID NO:10. The cysteine residue was placed at the C-terminal end of the peptide to enhance its antigenicity. The designed synthetic peptide served as an efficient antigen and the antibodies raised against the peptide showed a very high titer value. The detailed protocol for the generation of HB-Ab can be obtained at the vendor's website (http://www.genscript.com/PolyExpress.html).

Purified HB-C2A was resolved on 15% SDS-PAGE under reduced conditions. The gel containing the HB-C2A was subjected to blot transfer for Western blot and in case of dot blot the proteins were directly spotted onto the membrane. Blotted/spotted nitrocellulose membrane was blocked using 5% skim milk in 1×TBS-T (10 mM tris, 100 mM NaCl, 0.05% Tween-20; pH 7.4) at room temperature for 1 hr. Subsequently, the membrane was washed with 0.2% BSA in 1×TBS-T and the primary antibodies, raised in rabbit against the HB tag, was added at 1:2500 dilution and incubated overnight at 4° C. Secondary antibody conjugated with alkaline phosphatase, which detects the IgG rabbit antibody, was added to the membrane at 1:2500 dilution and incubated for 2 hours at 4° C. The band on the membrane was detected using the NBT/BCIP (Nitro-blue tetrazolium/5-Bromo-4-chloro-3-indolyl phosphate) substrate within 60 seconds of exposure.

IV. Separation Media and Methods of Use

In a further aspect, separation media are described herein which can be used in the purification of protein compositions. A separation medium described herein comprises a support phase and a stationary phase attached to the support phase, the stationary phase including an amino acid sequence comprising a repeating amino acid unit of BXXX-BXX, wherein B is an amino acid selected from the group consisting of histidine, lysine and arginine and X is an amino acid selected from the group consisting of amino acids other than histidine, lysine and arginine. The amino acid unit can be repeated at least three times in the amino acid sequence. In some embodiments, for example, the amino acid sequence includes the sequence of SEQ ID NO:1 or SEQ ID NO:2. In other embodiments, the stationary phase can include an amino acid sequence selected from Table I. The amino acid sequence of the stationary phase can be operable to selectively bind heparin.

The amino acid sequence of the stationary phase can be attached to the support phase through any suitable spacer not inconsistent with the objectives of the present invention. In some embodiments, a spacer comprises a hydrocarbon section. A hydrocarbon section can be a linear or branched $C_4$ to $C_{20}$ hydrocarbon. Further, the spacer can comprises one or more functionalities for reacting with the N-terminal and/or C-terminal ends of the stationary phase amino acid sequence. For example, the spacer can be activated by treatment with N-hydroxysuccinimide to form a stable amide linkage with the N-terminal end of the stationary phase amino acid sequence. In some embodiments, suitable support for attaching the amino acid sequence of the stationary phase is commercially available from GE Healthcare Life Sciences as NHS-activated Sepharose 4 Fast Flow. Alternatively, in some embodiments, the amino acid sequence of the stationary phase is attached directly to the support without an intervening spacer.

Employing a stationary phase comprising an amino acid sequence described herein can render the separation media operable for purification of heparin. The amino acid sequence, for example, can selectively bind heparin from a mixture of other species. The bound heparin fraction can be subsequently eluted with a salt gradient as detailed in Section III and Table II herein. For example, beef-lung and porcine intestinal mucosa are rich sources of heparin. The filtered tissue homogenates can be subjected to several cycles of ammonium sulfate treatment(s) to selectively eliminate proteins present in the tissue homogenates. The supernatant(s) obtained after several cycles of ammonium sulfate treatment, are dialyzed against 10 mM phosphate buffer containing 50 mM NaCl. Heparin present in the dialyzed supernatant is can be purified on a separation medium wherein NHS Sepharose 4 Fast Flow affinity matrix is modified or tagged with an amino acid sequence described herein, such as SEQ ID NO:1 or SEQ ID NO:2. NaCl salt gradient is used to elute the bound heparin fraction and elution monitored by 232 nm absorbance.

Sequence Listing Free Text

Designed amino acid sequence to act as an affinity tag for binding heparin.

Designed amino acid sequence to act as an affinity tag for binding heparin.

Designed nucleic acid for coding the amino acid sequence of SEQ ID No.: 1.

Designed nucleic acid for coding the amino acid sequence of SEQ ID No.: 2.

Designed amino acid sequence to act as an affinity tag for binding heparin.

Designed amino acid sequence to act as an affinity tag for binding heparin.

Designed nucleic acid for coding the amino acid sequence of SEQ ID No.: 5.

Designed nucleic acid for coding the amino acid sequence of SEQ ID No.: 6.

Designed amino acid sequence to produce polyclonal antibodies against an affinity tag for binding heparin.

The invention claimed is:

1. An affinity tag for protein purification comprising:

an amino acid sequence that comprises the sequence of SEQ ID NO:1.

2. The affinity tag of claim 1, wherein the affinity tag binds heparin.

3. An affinity tag for protein purification comprising:

an amino acid sequence that comprises the sequence of SEQ ID NO:2.

4. The affinity tag of claim 3, wherein the affinity tag binds heparin.

* * * * *